(12) United States Patent
Leonhardt

(10) Patent No.: US 12,295,721 B2
(45) Date of Patent: May 13, 2025

(54) SYSTEM AND METHOD FOR IDENTIFYING AND/OR MEASURING A SUBSTANCE CONCENTRATION IN THE EXHALED BREATH OF A PATIENT

(71) Applicant: Fresenius Vial SAS, Brézins (FR)

(72) Inventor: Jürgen Leonhardt, Berlin (DE)

(73) Assignee: Fresenius Vial SAS, Brézins (FR)

( * ) Notice: Subject to any disclaimer, the term of this patent is extended or adjusted under 35 U.S.C. 154(b) by 861 days.

(21) Appl. No.: 17/258,672

(22) PCT Filed: Jun. 5, 2019

(86) PCT No.: PCT/EP2019/064589
§ 371 (c)(1),
(2) Date: Jan. 7, 2021

(87) PCT Pub. No.: WO2020/011450
PCT Pub. Date: Jan. 16, 2020

(65) Prior Publication Data
US 2021/0267477 A1    Sep. 2, 2021

(30) Foreign Application Priority Data

Jul. 9, 2018 (EP) ..................................... 18305905

(51) Int. Cl.
*A61B 5/08* (2006.01)
*G01N 1/22* (2006.01)
(Continued)

(52) U.S. Cl.
CPC ........... *A61B 5/082* (2013.01); *G01N 1/2205* (2013.01); *G01N 27/622* (2013.01); *G01N 30/20* (2013.01);
(Continued)

(58) Field of Classification Search
CPC .... A61B 5/082; G01N 1/2205; G01N 27/622; G01N 30/20; G01N 33/497;
(Continued)

(56) References Cited

U.S. PATENT DOCUMENTS 5,855,650 A * 1/1999 Kalbassi ............... F25J 3/04169
                                                        95/120
2003/0139681 A1 * 7/2003 Melker ................. A61B 5/0836
                                                        600/532
(Continued)

FOREIGN PATENT DOCUMENTS

CN        1878604 A     12/2006
CN      101600960 A     12/2009
(Continued)

OTHER PUBLICATIONS

International Search Report and Written Opinion for International Application No. PCT/EP2019/064589 Dated Aug. 21, 2019.
(Continued)

*Primary Examiner* — Alex M Valvis
*Assistant Examiner* — Anna Roberts
(74) *Attorney, Agent, or Firm* — Cook Alex Ltd.

(57) ABSTRACT

A system for identifying and/or measuring a substance concentration in the exhaled breath of a patient (4), comprises a measurement apparatus (20) for performing an ion mobility spectrometry measurement of a sampling gas stream (A) obtained from the exhaled breath of the patient (4), the measurement apparatus (20) comprising a drift detector (22) and at least one gas circuit (23, 24) connected to the drift detector (22) for guiding an analytic gas stream (B), into which a sample of the sampling gas stream (A) is injectable, towards an inlet end (220) of the drift detector (22) and/or a drift gas stream (C) towards an outlet end (221) of the drift detector (22), wherein the at least one gas circuit
(Continued)

(23, 24) comprises a molecular sieve filter (233, 241) comprising a filter material (26) for filtering the analytic gas stream (B) and/or the drift gas stream (C). Herein, the filter material (26) comprises the zeolite NaY. In this way a system for measuring a substance concentration in the exhaled breath of a patient is provided which allows for accurate measurements using the ion mobility spectrometry (IMS).

15 Claims, 3 Drawing Sheets

(51) Int. Cl.
| | | |
|---|---|---|
| *G01N 27/622* | (2021.01) | |
| *G01N 30/02* | (2006.01) | |
| *G01N 30/20* | (2006.01) | |
| *G01N 30/72* | (2006.01) | |
| *G01N 33/497* | (2006.01) | |

(52) U.S. Cl.
CPC ..... *G01N 33/497* (2013.01); *G01N 2030/025* (2013.01); *G01N 2030/207* (2013.01); *G01N 2030/7226* (2013.01)

(58) Field of Classification Search
CPC ....... G01N 2030/025; G01N 2030/207; G01N 2030/7226; G01N 2033/4975
See application file for complete search history.

(56) References Cited

U.S. PATENT DOCUMENTS

| | | |
|---|---|---|
| 2005/0065446 A1 | 3/2005 | Talton |
| 2007/0062255 A1 | 3/2007 | Talton |
| 2010/0212668 A1 | 8/2010 | Flanagan et al. |
| 2012/0277612 A1 | 11/2012 | Li |
| 2013/0211211 A1* | 8/2013 | Sato .................. A61B 10/0045 600/309 |
| 2020/0275883 A1* | 9/2020 | Lindner .............. G01N 33/497 |

FOREIGN PATENT DOCUMENTS

| | | | |
|---|---|---|---|
| DE | 19856784 B4 | 6/2000 | |
| DE | 10228912 C1 | 11/2003 | |
| EP | 0573060 A2 * | 6/1993 | ......... A61B 5/0836 |
| JP | H0647047 A | 2/1994 | |
| JP | H07284488 A | 10/1995 | |
| JP | H11271302 A | 10/1999 | |
| JP | 2009047593 A | 3/2009 | |
| JP | 2014001109 A | 1/2014 | |

OTHER PUBLICATIONS

Australian Patent Office Examination Report No 1 AU Application No. AU2019299907 (AU Counterpart to U.S. Appl. No. 17/258,672)(date of mailing Dec. 2, 2024).

Chinese Patent Office First Official Examination Opinion with translation CN Application No. 2019800453233 (CN Counterpart to U.S. Appl. No. 17/258,672) (date of mailing Jan. 15, 2024).

Chinese Patent Office Notification of Grant Patent Rights for Invention with translation CN Applicaiton No. 2019800453233 (CN Counterpart to U.S. Appl. No. 17/258,672) (date of mailing Apr. 11, 2024).

Japanese Patent Office Written Opinion of Refusal with translation JP Application No. 2021500203 to (JP Counterpart to U.S. Appl. No. 17/258,672) (date of mailing Jul. 13, 2023).

Japanese Patent Office Decision to Grant a Patent with translation JP Application No. 2021500203 (JP Counterpart to U.S. Appl. No. 17/258,672) (date of mailing Aug. 28, 2023).

* cited by examiner

SYSTEM AND METHOD FOR IDENTIFYING AND/OR MEASURING A SUBSTANCE CONCENTRATION IN THE EXHALED BREATH OF A PATIENT

CROSS-REFERENCE TO RELATED APPLICATION

The present application is a U.S. National Stage of PCT International Patent Application No. PCT/EP2019/064589, filed Jun. 5, 2019, which claims priority to EP application Ser. No. 18/305,905.4, filed Jul. 9, 2018, both of which are hereby incorporated herein by reference.

DESCRIPTION

The invention relates to a system for identifying and/or measuring a substance concentration in the exhaled breath of a patient according to the preamble of claim 1 and to a method for measuring a substance concentration in the exhaled breath of a patient.

A system of this kind comprises a measurement apparatus for performing an ion mobility spectrometry measurement of a sampling gas stream obtained from the exhaled breath of the patient. The measurement apparatus herein comprises a drift detector and at least one gas circuit connected to the drift detector for guiding an analytic gas stream, into which a sample of the sampling gas stream is injectable, towards an inlet end of the drift detector and/or a drift gas stream towards an outlet end of the drift detector. Herein, the at least one gas circuit comprises a molecular sieve filter comprising a filter material for filtering the analytic gas stream and/or the drift gas stream.

Mechanical ventilation is used in conventional general anesthesia procedures for example in an operating center or during long-term sedation procedures for critically ill patients in an intensive care unit of a hospital. In the context of such general anesthesia procedures patients are intubated with endo-tracheal catheters to on the one hand provide for a ventilation and on the other hand administer gaseous anesthetic agents.

As an alternative to inhalational anesthesia procedures using gaseous anesthetic agents, in the context of intravenous anesthesia an anesthetic agent such as Propofol is administered intravenously into a patient, for example in the context of a so-called total intravenous anesthesia (TIVA) procedure. Such intravenous anesthesia may also be preferable for example for a long-term sedation procedure in an intensive care unit.

In particular in the context of intravenous anesthesia for example using Propofol as an anesthetic agent, it is of substantial interest to be able to monitor the concentration of the anesthetic agent in the patient's body and its related effects in particular with regard to the anesthetic impact. Generally, conclusions with regard to the drug concentration in the patient's body can be drawn by monitoring the presence and concentration of an anesthetic agent and related substances in the exhaled air of a patient. Using a suitable modeling, for example a pharmacokinetic/pharmacodynamic model, the drug concentration in the patient's body can be predicted from the drug concentration in the exhaled air. Such predictions however require on the one hand precise models and on the other hand a precise measuring of substance concentration in the exhaled air.

It has been proposed to use gas chromatography ion mobility spectrometry (GC-IMS) for the detection of a substance, in particular when using an anesthetic agent such as Propofol, in the exhaled breath of a patient for monitoring during an anesthesia procedure. Within ion mobility spectrometry, components of a gas sample are ionized by means of an ion molecule reaction and are injected into an electrical drift field of a drift detector. By applying a substantial electrical field strength, for example several hundred volts per centimeter, to the drift detector, the ionized components are driven towards a detector which is constituted to generate a measurement signal upon arrival of the ionized components. The ionized components encounter an opposing force whilst travelling through the drift detector, which originates from a drift gas that flows through the same drift detector, but in an opposing direction, thus effectively presenting an obstacle for the ionized components depending on for example their shape and cross section.

Generally, the drift time of the ionized components through the drift detector depends on the applied voltage, on the temperature and pressure in the drift detector, on the mass of the ionized components, their shape and charge and the like, such that different components exhibit different velocities and hence will travel through the drift detector in different drift times. Different ionized components hence will arrive at the detector at different times, such that signals separated in time and relating to the different ionized components can be detected at the detector, giving rise to a so-called drift spectrum (signal intensity over drift time) containing peaks relating to different components of the gas sample.

Within the GC-IMS, the ion mobility spectrometry is combined with a gas chromatography in which, prior to injecting an analytic gas stream into the drift detector, the analytic gas stream is guided through a separation column forming a capillary column in which different components of the analytic gas stream are separated from one another because different components travel through the separation column in different travel times (so-called retention times, which are indicative of the time a specific component remains in the separation column) due to their chemical properties. By means of the gas chromatography different components of the analytic gas stream enter into the drift detector at different times such that the components are separated prior to entering the drift detector, which improves the specifity of the components and hence their identification in a measured drift spectrum A gas chromatography ion mobility spectrometry (GC-IMS) system is for example known from DE 198 56 784 B4 and DE 102 28 912 C1.

To determine the concentration of a substance of interest in the patient's breath, for example an anesthetic agent, in particular Propofol, a peak in a drift spectrum relating to the substance of interest may be identified, and from the peak's height conclusions may be drawn with respect to the concentration of the substance of interest in the gas sample taken from the exhaled breath of the patient. Generally, using a suitable calibration the peak's height may be related to the concentration of the substance of interest, such that from the peak's height the concentration may be directly evaluated.

However, concentration values typically lie in the parts-per-billion (ppb) range such that the detected signals may interfere with certain contaminations in the analytic gas stream and the drift gas stream. The accuracy of the concentration measurements hence is sensitive in particular with respect to a contamination in the analytic gas stream and the drift gas stream. In particular it is to be ensured that the analytic gas stream as well as the drift gas stream does not comprise any remaining Propofol content and in addition has a very low water content (e.g., below 1 ppm).

For this, it has been proposed to use molecular sieve (also called mol sieve) filters which serve to both remove Propofol from the associated gas stream as well as reduce the water content in the gas stream by adsorption.

Because water is collected within the molecular sieve filter over time, the filter performance may degrade over time, making it necessary to periodically exchange and regenerate the filter. Herein it is desirable to use filters having a long durability, hence providing for a long time-of-use prior to making a replacement and regeneration of the filter necessary.

It is an object of the instant invention to provide a system and method for measuring a substance concentration in the exhaled breath of a patient which allow for accurate measurements using the ion mobility spectrometry, in particular the gas chromatography ion mobility spectrometry (GC-IMS).

This object is achieved by means of a system comprising the features of claim 1.

Accordingly, the filter material of the molecular sieve filter comprises the zeolite NaY.

The filter material hence is, fully or in part, made up of a zeolite material, namely NaY.

Conventionally, zeolites are grouped by classes indicative of their type of structure. The zeolite material used as filter material in the instant matter belongs to the class "Y".

Zeolites of the class "Y" are synthetically produced crystalline substances having a crystalline structure consisting of so-called sodalite cages connected to each other by means of hexagonal prisms. In this way pores of regular shape and size are formed, the largest poor having a diameter of approximately 7 A (Angstrom), corresponding to approximately 0.7 nm.

"Na" indicates the modification of the structure of the zeolite, NaY being also denoted as "the zeolite Y of the Na form". Within NaY Natrium iones are embedded into the crystalline structure of Y zeolite.

NaY in the instant context may be used as filter material in different forms, for example in the form of binder containing granules or binderfree granules (in the latter case being denoted also as NaY BFK).

The filter material comprising or consisting of NaY, for example in the shape of granules, exhibits a rather large dynamic adsorption capacity to adsorb water, for example between 20% and 30%, for example around 25%.

The NaY filter material may have a pore size between 0.6 nm and 0.8 nm, for example 0.7 nm, corresponding to about 7 A.

With the NaY filter material it has-surprisingly-been found that a removal of a substance of interest, in particular Propofol, as well as a removal of water from a gas stream can efficiently be achieved, the filter material providing for the possibility to construct a filter having a large water adsorption capacity and hence providing for a filter allowing for a long time-of-use, for example a time-of-use longer than a year.

The molecular sieve filter may for example have a cylindrical shape with a diameter in a range between 1 cm and 10 cm, for example in the range between 3 cm and 6 cm. This filter may for example be 10 to 20 cm long, the molecular sieve filter comprising a housing encompassing the filter material, the housing being made for example of a stainless steel material. The volume of the filter is filled with the NaY filter material, the gas stream to be filtered in operation passing through the filter material in order to remove water and a desired substance of interest, in particular Propofol, from the gas stream.

In one embodiment the at least one gas circuit comprises a molecular sieve filter both in a portion in which (solely) the analytic gas stream is guided and in a portion in which a combined gas stream of the analytic gas stream and the drift gas stream is guided, each molecular sieve filter comprising an NAY filter material for filtering the associated gas stream. Herein, the at least one gas circuit may in addition comprise another filter device, for example a charcoal filter, for providing for example a further filtering of the analytic gas stream in respect of organic compounds.

In one embodiment, the at least one gas circuit comprises one or multiple fluid lines which at least partially are made of a PTFE material for guiding the analytic gas stream and/or the drift gas stream. The fluid lines may be fully made from a PTFE material, or they may comprise a coating of a PTFE material, hence preventing a forming of water droplets on the inside of the fluid lines. The fluid lines may for example comprise an inner diameter in the range between 1 mm and 3 mm, for example 2 mm.

In one embodiment, a portion of the at least one gas circuit embodied to guide the analytic gas stream comprises a separation column for chromatographically separating components of the analytic gas stream from each other prior to injecting the analytic gas stream into the inlet end of the drift detector. The ion mobility spectrometry hence is combined with a gas chromatography in order to provide for a pronounced separation of components of the gas stream to be analyzed. Prior to being injected into the drift detector the analytic gas stream passes through the separation column, the separation column having for example a capillary channel length in between 0.5 m and 5 m, for example at about 1 m. The inner walls forming the capillary channel of the separation column for example comprise a liquid phase providing for different retention times of different components within the separation column such that different components of the analytic gas stream require different times to travel through the separation column. Hence, different components of the analytic gas stream are injected into the drift detector at different times, such that the components are separated already prior to injecting them into the drift detector. Upon traveling through the drift detector and upon further separation within the drift detector the different components are detected by a suitable detection circuitry at the outlet end of the drift detector, allowing for a detection of the different components within the analytic gas stream and a measuring of the concentration by measuring a peak height of a peak in a detected signal associated with a substance of interest, in particular Propofol.

The separation column beneficially is heated to a predefined temperature, in particular to a temperature above 80° C., for example above 85° C., in order to provide for a suitable difference in retention times between different components of the analytic gas stream, in particular the retention times of water ($H_2O$) and Propofol.

By using a gas chromatography in combination with the ion mobility spectrometry fast measurement times may be achieved, for example allowing for a reliable measurement of the concentration of a substance of interest in the patient's breath, in particular Propofol, with a measurement time below 1 minute.

In one embodiment, the system comprises an additional sampling gas circuit for guiding a sampling gas stream taken from the patient's breath. From the sampling gas stream samples are taken and are injected into the analytic gas stream by means of a valve device, the valve device being switchable such that samples of the sampling gas stream (having for example a volume of 1 ccm) can be injected into the analytic gas stream by connecting the at least one gas circuit to the sampling gas circuit via the valve device.

In one embodiment, also the sampling gas circuit comprises one or multiple fluid lines at least partially made of a PTFE material for guiding the sampling gas stream, the sampling gas circuit for example being connected to a catheter device through which ventilation of the patient is provided. The fluid lines may be fully made of a PTFE material, or they may comprise a PTFE coating or the like.

In one embodiment, the at least one gas circuit comprises a first pump device for pumping the analytic gas stream towards the inlet end of the drift detector. The pump device may for example be a membrane pump. The first pump device may be placed in particular, when looked at along the streaming direction of the analytic gas stream, within the at least one gas circuit at a location prior to the separation column such that the first pump device effects a pressure for moving the analytic gas stream through the separation column towards the inlet end of the drift detector.

In one embodiment, the at least one gas circuit comprises a second pump device for pumping a combined gas stream of the drift gas stream and the analytical gas stream, the second pump device for example also being a membrane pump. By means of the membrane pump the combined gas stream may in particular be pumped towards a splitter, which splits the combined gas stream into the analytic gas stream and the drift gas stream, the drift gas stream then being guided towards the outlet end of the drift detector for drifting through the drift detector in a direction opposite to ionized components stemming from the analytic gas stream injected into the drift detector at the inlet end. The drift gas stream drifting through the drift detector beneficially is comprised of clean air.

In one embodiment, the at least one gas circuit forms a closed circuit for guiding the analytic gas stream respectively the drift gas stream. Hence, the analytic gas stream and the drift gas stream flow through the at least one gas circuit in a closed loop, such that no feeding of a gas from external sources in particular into the gas circuit is required. The respective gas stream flows through the gas circuit in a closed loop, the respective gas being cleaned by means of the associated filter device after passing through the drift detector before again being injected into the drift detector. Herein, a sample of sample gas of the exhaled breath is injected into the analytic gas stream prior to passing the separation column and prior to be injected into the drift detector in order to measure a substance concentration in the sample.

By means of the system, characteristic values relating to one or multiple drift spectra may be determined, which may then be used, using a suitable calibration, to output a concentration estimate indicative of substance concentrations in the gas sample. The substance(s) of interest may in particular be at least one anesthetic agent, for example Propofol, such that the system may in particular be suitable for providing a monitoring during an anesthesia or sedation procedure, for example an anesthesia procedure in which an anesthetic agent is intravenously administered to a patient and the concentration of the anesthetic agent in the patient's body is monitored using ion mobility spectrometry on a gas sample of the exhaled breath of the patient.

For this, gas samples may be taken continuously or periodically in order to monitor the concentration(s) of at least one anesthetic agent, in particular Propofol, in the exhaled breath of a patient.

The object is also achieved by a method for measuring a substance concentration in the exhaled breath of a patient, comprising: obtaining a sampling gas stream from the exhaled breath of the patient, and performing, by means of a measurement apparatus, an ion mobility spectrometry measurement of the sampling gas stream, the measurement apparatus comprising a drift detector and at least one gas circuit connected to the drift detector for guiding an analytic gas stream, into which a sample of the sampling gas stream is injectable, towards an inlet end of the drift detector and/or a drift gas stream towards an outlet end of the drift detector, wherein the at least one gas circuit comprises a molecular sieve filter comprising a filter material for filtering an associated gas stream. Herein, the filter material comprises the zeolite NaY.

The advantages and advantageous embodiments described above for the system equally apply also to the method, such that it shall be referred to the above.

The idea underlying the invention shall subsequently be described in more detail with reference to the embodiments shown in the drawings. Herein:

Figure 3:
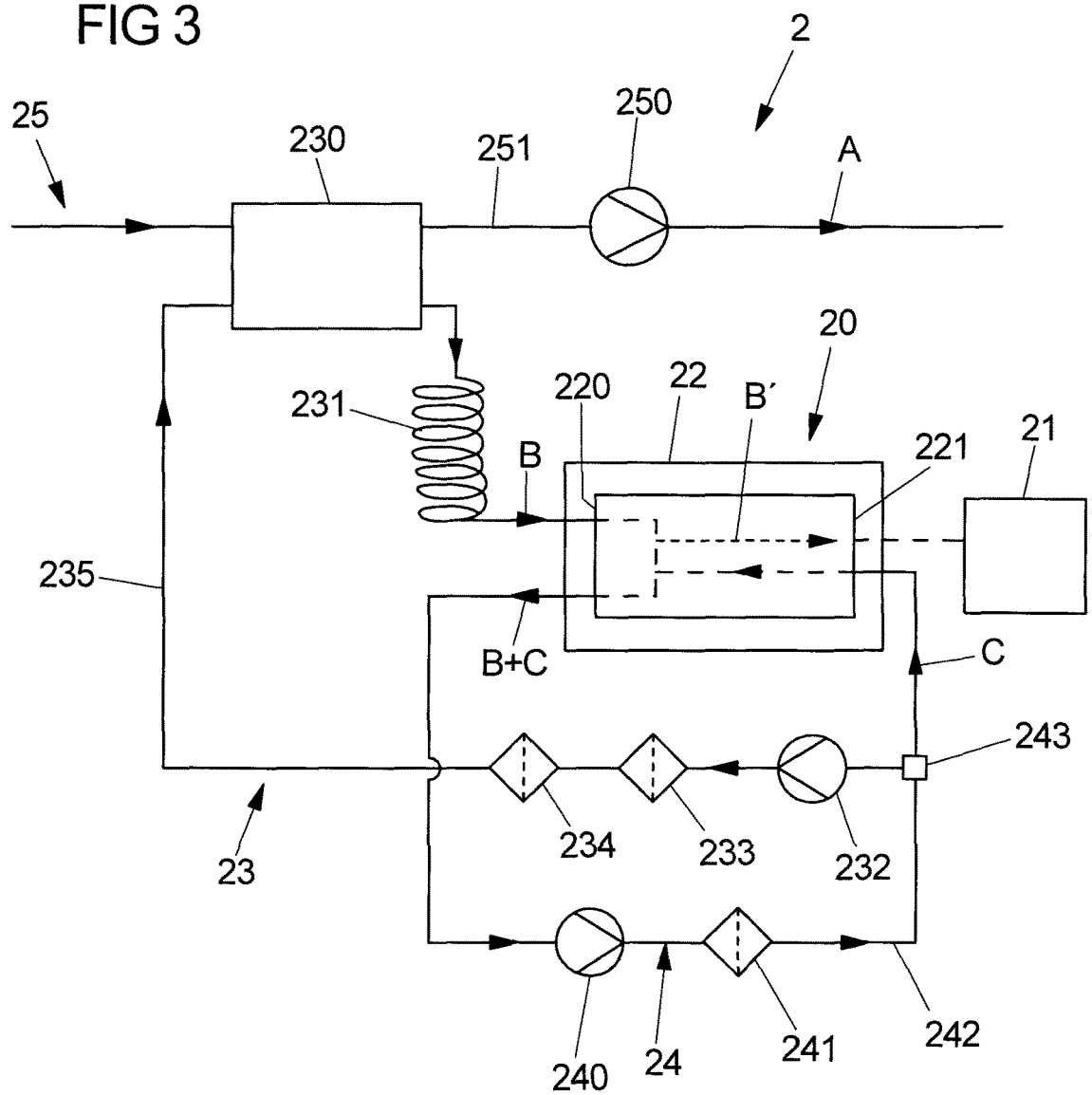
Figure 4:
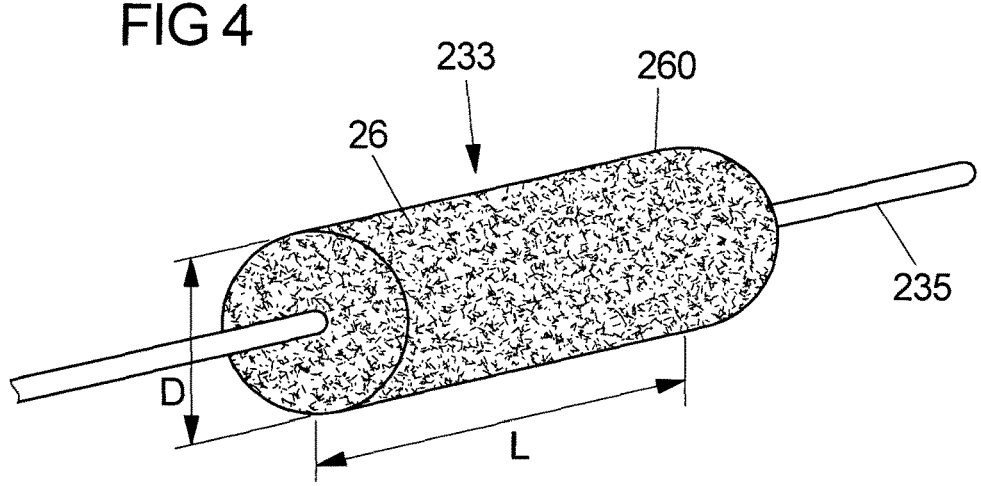

FIG. 3 a schematic drawing of the layout of a system for measuring a substance concentration in the extent breath of a patient; and FIG. 4 a schematic drawing of a filter device for filtering an associated gas stream.

Figure 1:
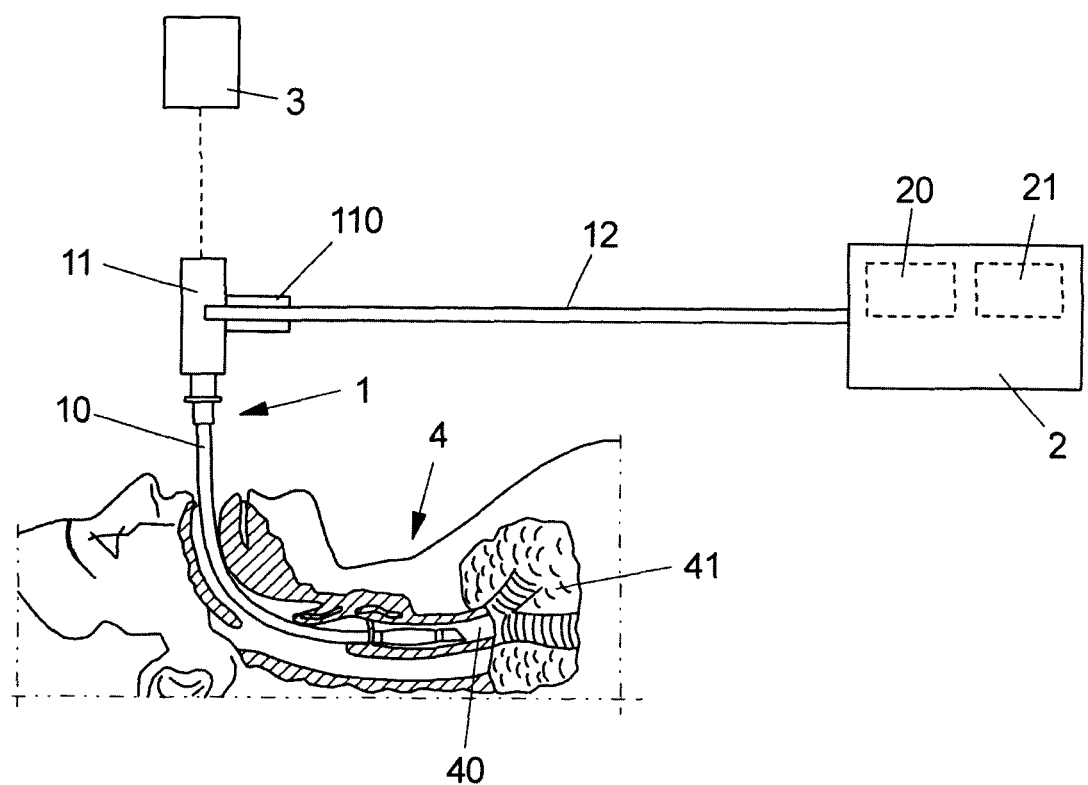
FIG. 1 shows a schematic view of a system comprising an endo-tracheal catheter and a ventilation system for providing ventilation to a patient.

FIG. 1 shows an embodiment of a system as it generally may be used for example in the context of an anesthesia procedure.

For example in an intravenous anesthesia procedure, an anesthetic agent such as Propofol is intravenously administered to a patient 4 and hence enters into the patient's bloodstream. In order to monitor the concentration of the anesthetic substance within the patient's body, a gas detector 2 connected in a side-stream arrangement to a connection piece 11 of an endo-tracheal catheter 1 continuously or periodically measures a drug concentration in a gaseous flow taken from the patient's lungs 41 via a catheter tube 10 of the endo-tracheal catheter 1 inserted into the trachea 40 of the patient 4 and potentially connected to a ventilation system 3 for providing a ventilation of the patient 4. By means of such concentration measurements, hence, a monitoring of the substance concentration in the exhaled air of the patient 4 may be conducted, allowing for conclusions with respect to the concentration of the anesthetic substance within the patient's body, for example using a suitable pharmacokinetic/pharmacodynamic model or the like.

In an embodiment, the gas detector 2 comprises a processing device 21 and a measurement apparatus 20, the measurement apparatus 20 being designed to conduct ion mobility spectrometry measurements on gas samples taken via a side-stream line 12 connected at a port 110 to the connection piece 11 of the endo-tracheal catheter 1.

By means of the side-stream line 12 gas samples may be taken in a continuous or periodic fashion from a gas flow streaming through the connection piece 11. In order to measure the concentration of a substance of interest in a gas sample taken from the exhaled breath of the patient 4, ion mobility spectrometry is used, in which components of the gas sample are ionized and injected into a drift detector, through which the components are driven by a substantial voltage, for example larger than 100 volt or even a few hundred volt per centimeter of drift, towards a detector. By means of the detector a measurement signal is obtained, generated by the ionized components arriving at the detector and causing a low voltage signal at the detector. Because different components exhibit different drift velocities through the drift detector—for example dependent on the temperature and pressure in the drift detector, the component's mass, and the component's shape and charge—different components will arrive at the detector at different drift times, causing a drift spectrum in which peaks occur relating to the different drift times of the different components. From the signal intensity at a peak relating to a specific component relating to a substance of interest, hence, conclusions can be drawn with regard to the concentration of the substance of interest in the gas sample taken from the gas flow.

In order to draw conclusions with regard to the substance concentration in the gas sample, characteristic values in relation to a drift spectrum are determined, such characteristic values allowing to infer a concentration estimate (by for example calibrating, in an initial calibration phase, a range of a characteristic value to a range of concentration values). Recorded data obtained from ion mobility spectrometry however generally is subject to noise, such that it may not be possible, without further ado, to accurately determine characteristic values such as the height of a peak relating to a substance of interest in a drift spectrum with sufficient accuracy.

Figure 2A:
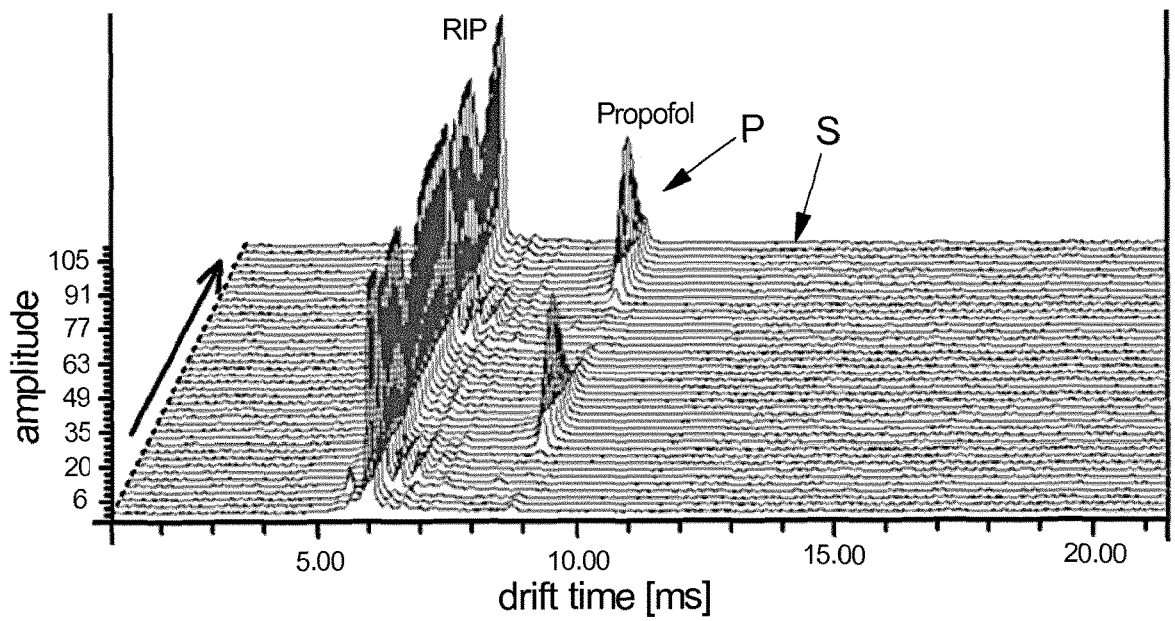
FIG. 2A shows a graphical representation of multiple drift spectra recorded for a sample taken from the exhaled breath of a patient over time by using GC-ion mobility spectrometry.
Figure 2B:
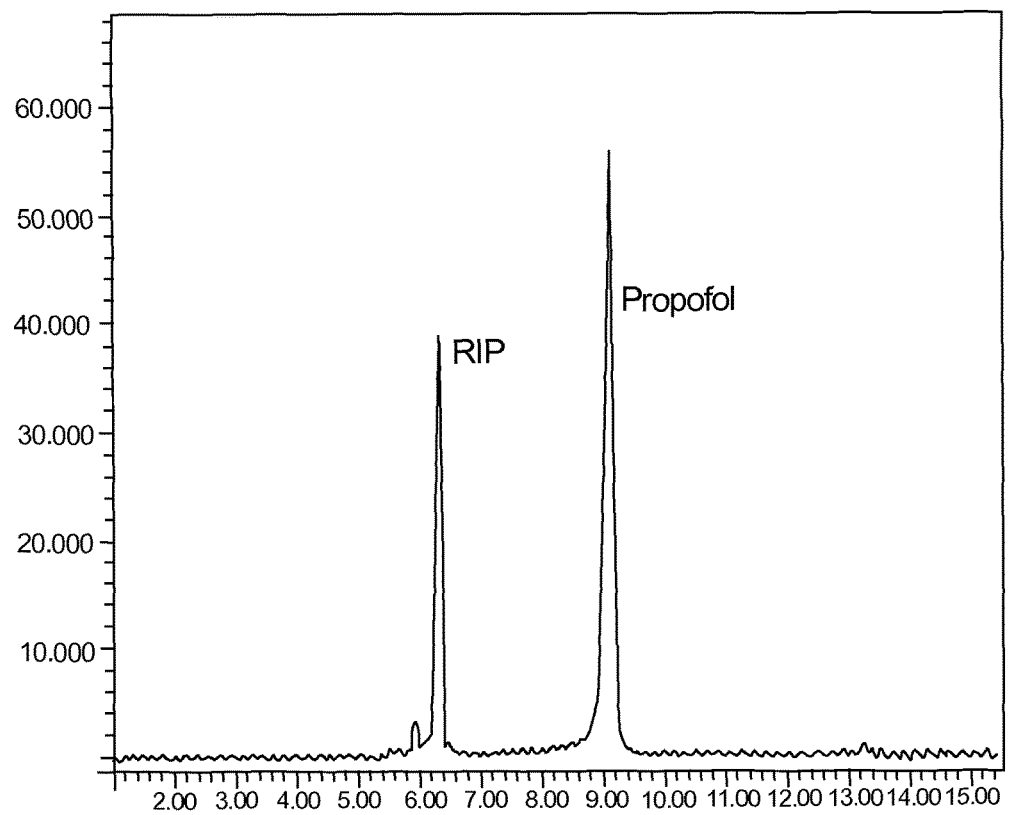
FIG. 2B shows a graphical representation of a combined drift spectrum obtained from the drift spectra of FIG. 2A.

FIGS. 2A and 2B show an example of a recorded drift spectra S obtained by an ion mobility spectrometry measurement using the measurement apparatus 20 of the gas detector 2. FIG. 2A herein shows multiple drift spectra S recorded over time for a sample taken from the exhaled breath of a patient 4, illustrating in particular how a peak relating to a substance of interest, in the instant case Propofol, evolves over time in the measured drift spectra S. FIG. 2B shows a combined drift spectrum S obtained (e.g. by summation), from the drift spectra of FIG. 2A. As it is visible in FIG. 2B, the resulting drift spectrum S contains various peaks, the different peaks relating to different components of the gas sample, a peak of interest P relating to for example Propofol.

FIG. 3 shows an embodiment of a layout of a detection device 2 having a measurement apparatus 20 and a processing device 21 for measuring the concentration of a substance of interest, in particular Propofol, in a sample of the exhaled breath of a patient by using ion mobility spectrometry information in combination with gas chromatography (so-called GC-IMS).

The measurement apparatus 20 comprises gas circuits for guiding different gas streams from and towards a drift detector 22.

A sampling gas circuit 25 by means of fluid lines 251 serves to guide a side-stream of the exhaled breath of a patient 4 (see FIG. 1) through a side-stream line 12 of a catheter device 1 towards the detection device 2, the sampling gas circuit 25 for example comprising a pump device 250 in the shape of a membrane pump for transporting a sampling gas stream A through the sampling gas circuit 25.

The sampling gas circuit 25 by means of a valve device 230 is connectable to an analytic gas circuit 23, the valve device 230 being switchable such that samples of the sampling gas stream A (having a volume of for example 1 ccm) flowing through the sampling gas circuit 25 may be injected into the analytic gas circuit 23 for analysis.

The analytic gas circuit 23, by means of fluid lines 235, guides an analytic gas stream B through a separation column 231 and from the separation column 231 towards the drift detector 22 for injection into the drift detector 22 at an inlet end 220. Components B' of the analytic gas stream B upon injection into the drift detector 22 at the inlet end 220 are ionized by means of an ionization radiation and, driven by a voltage applied to the drift detector 22, drift through the drift detector 22 towards an outlet end 221, at which the time of arrival of the ionized components B' is registered by a suitable detection circuitry to obtain drift spectra as illustrated in FIG. 2 and is analyzed by means of the processing device 21.

The separation column 231 provides for a separation of components of the analytic gas stream B prior to injection into the drift detector 22. The separation column 231 provides for a gas chromatography by forming a capillary column having a length of for example between 0.5 m and 5 m, for example in the range of 1 m, and having an inner diameter for example between 0.1 mm and 1 mm, for example around the 0.5 mm. Within the capillary column a liquid phase providing for a retention of components within the capillary column is provided, the liquid phase causing different retention times for different components within the capillary column such that components exit the separation column 231 at different times due to their distinct retention times.

Hence, when the analytic gas stream B is injected into the drift detector 22, relevant components B' of the analytic gas stream B are already separated in time, the drifting through the drift detector 22 due to the ionization and the driving voltage providing for a further separation of the components B', the ionized components B' then being detectable by means of a suitable detection circuitry at the outlet end 221 in connection with the processing circuitry 21.

Such gas portions of the analytic gas stream B which are not ionized exit the drift detector 22 at the inlet end 220 and enter into a drift gas circuit 24 in which the analytic gas stream B is guided together with a drift gas stream C. By means of the drift gas circuit 24 the combined gas stream of the analytic gas stream B and the drift gas stream C is guided towards a splitter 243, at which the analytic gas stream B and the drift gas stream C are split, the drift gas stream C in the shape of clean air being guided towards the outlet end 221 of the drift detector 22 and being injected into the drift detector 22 at the outlet end 221, such that the drift gas stream C flows through the drift detector 22 in a direction opposite to the ionized components B' of the analytic gas stream B drifting through the drift detector 22 driven by the applied electric field in order to provide for a (constant) counter flow for the ionized components within the drift detector 22. The drift gas circuit 24 comprises a pump device 240 in the shape of a membrane pump for driving the combined gas stream of the analytic gas stream B and the drift gas stream C and a filter device 241 in the shape of a molecular sieve filter. Fluid lines 242 serve to guide the combined gas stream towards and from the drift detector 22, the drift gas stream C flowing via the splitter 243 towards the outlet end 221 of the drift detector 22 for injection into the drift detector 22.

After having been separated from the drift gas stream C by means of the splitter 243, the analytic gas stream B is driven by a pump device 232 in the shape of a membrane pump through filter devices 233, 234, the filter device 233 being shaped as a molecular sieve filter and the filter device 234 as a charcoal filter for cleaning the analytic gas stream B from water and from substances, in particular Propofol. The analytic gas stream B (now being present as substantially clean air) then once more enters the valve device 230 via which a sample of the sampling gas stream A is injectable into the analytic gas stream B.

The fluid lines 235, 242, 251 of the system each may be, fully or at least partially, made of a PTFE material. For example, the fluid lines 235, 242, 251 may be fully made from a PTFE material. Alternatively, the fluid lines 235, 242, 251 may comprise a PTFE coating at their inside. By such choice of material a forming of water droplets within the fluid lines 235, 242, 251 may be prevented.

Within the analytic gas circuit 23 the analytic gas stream B is cleaned prior to flowing through the valve device 230 and hence prior to taking up (another) sample of the sampling gas stream A for analysis by means of the separation column 231 and the drift detector 22. In particular, prior to injecting another sample of the sampling gas stream A into the analytic gas stream B the analytic gas stream B is cleaned from water and from the substance of interest, namely Propofol, such that the analytic gas stream B is substantially free of water and Propofol prior to flowing through the valve device 230. This is necessary in order to obtain an accurate measurement result for the concentration of Propofol in the analytic gas stream B being indicative of the Propofol concentration in the breath of the patient 4.

In addition, also the drift gas stream C must be substantially free of water and the substance of interest, namely Propofol.

For this, both the analytic gas circuit 23 and the drift gas circuit 24 comprise a filter device 233, 241 in the shape of a molecular sieve filter as schematically indicated in FIG. 4, the filter device 233, 241 comprising a housing 260 for example being made of a stainless steel material encompassing a filter material 26 comprising or consisting of NaY.

The zeolite NaY filter material 26 provides for a removal of water and Propofol from the respective gas stream and exhibits a large water adsorption capacity, hence allowing for a rather long time-of-use of the system prior to a replacement of the filter devices 233, 241.

The zeolite Na Y may be used in the shape of granules, wherein binder containing granules or binderfree granules (NaY BFK) may be used.

In particular, by using such filter material it can be provided that the water content in the respective gas stream remains below one part per million, the substance of interest (Propofol) being substantially completely removed from the respective gas stream.

The molecular sieve filter, as illustrated in FIG. 4, has a cylindrical shape having a diameter D of for example in between 1 cm and 10 cm, in particular between 3 cm and 6 cm, and a length L for example between 10 cm and 20 cm. The volume of the filter device is filled with the filter material 26, the dimensions D, L of the filter being chosen according to a required volume for obtaining a desired filter performance.

In the embodiment shown in FIG. 3, the analytic gas circuit 23 and the drift gas circuit 24 are formed as a combined gas circuit, which represents a closed circuit. The separation column 231 of the analytic gas circuit 23 herein is heated up to a temperature above 80° C., beneficially above 85° C., hence providing for an effective separation of components within the capillary column formed by the separation column 231.

The idea underlying the invention is not limited to the embodiments described above, but may be implemented in an entirely different fashion.

By means of the proposed design a compact system may be provided allowing for a measurement of the concentration of a substance of interest, in particular Propofol, in the patient's breath with a measurement time below 1 minute, hence making an online inspection and control for example in the context of an anesthesia procedure possible.

LIST OF REFERENCE NUMERALS

1 Endo-tracheal catheter
10 Catheter tube
11 Connection piece
110 Port
12 Side-stream line
2 Detection device
20 Measurement apparatus
21 Processing device
22 Drift detector
220, 221 End
23 Analytic gas circuit
230 Valve device
231 Separation column
232 Pump device
233 Filter device (mol sieve filter)
234 Filter device (charcoal filter)
235 Lines
24 Drift gas circuit
240 Pump device
241 Filter device (mol sieve filter)
242 Lines
243 Splitter
25 Sampling gas circuit
250 Pump device
251 Lines
26 Zeolite filter material
260 Housing
3 Ventilation system
4 Patient
40 Trachea
41 lungs
A Sampling gas stream
B Analytic gas stream
B' Ionized components
C Drift gas stream
D Diameter
L Length
P Peak of interest (Propofol)
S Drift spectrum

The invention claimed is:

1. A system for identifying and/or measuring a substance concentration in an exhaled breath of a patient, comprising:
a measurement apparatus for performing an ion mobility spectrometry measurement of a sampling gas stream (A) obtained from the exhaled breath of the patient, the measurement apparatus comprising a drift detector and at least one gas circuit connected to the drift detector for guiding an analytic gas stream (B), into which a sample of the sampling gas stream (A) is injectable, the analytic gas stream (B) is injectable towards an inlet end of the drift detector and a drift gas stream (C) is injectable towards an outlet end of the drift detector, wherein the at least one gas circuit comprises a molecular sieve filter comprising a filter material for filtering the analytic gas stream (B) and the drift gas stream (C), wherein the filter material comprises zeolite NaY and wherein the at least one gas circuit forms a closed circuit for guiding the analytic gas stream (B) and the drift gas stream (C) in a closed loop, wherein the analytic gas stream and the drift gas stream are cleaned by the molecular sieve filter after passing through the drift detector before again being injected into the drift detector.

2. The system according to claim 1, wherein the filter material comprises NaY binder containing granules or NaY binderfree granules.

3. The system according to claim 1 wherein the zeolite NaY filter material has a pore size between 0.6 nm and 0.8 nm.

4. The system according to claim 1 wherein the molecular sieve filter has a cylindrical shape with a diameter between 1 cm and 10 cm.

5. The system according to claim 1 wherein the molecular sieve filter comprises a housing encompassing the filter material, the housing being made of a stainless steel.

6. The system according to claim 1 wherein the at least one gas circuit comprises a fluid line at least partially made of polytetrafluoroethylene (PTFE) for guiding the analytic gas stream (B) and the drift gas stream (C).

7. The system according to claim 1 wherein the at least one gas circuit comprises a separation column for chromatographically separating components of the analytic gas stream (B) from each other prior to injecting the analytic gas stream (B) into the inlet end of the drift detector.

8. The system according to claim 7, wherein the separation column forms a capillary channel for guiding the analytic gas stream (B) having a length between 0.5 m and 5 m.

9. The system according to claim 1 wherein the system further includes a sampling gas circuit for guiding said sampling gas stream (A) taken from exhaled breath of the patient and a valve device, the at least one gas circuit being connectable to the sampling gas circuit by means of the valve device for injecting a sample of the sample gas stream (A) into the analytic gas stream (B).

10. The system according to claim 9, wherein the sampling gas circuit comprises a fluid line at least partially made of polytetrafluoroethylene PTFE for guiding the sampling gas stream (A).

11. The system according to claim 1 wherein the at least one gas circuit comprises a first pump device for pumping the analytic gas stream (B) towards the inlet end of the drift detector.

12. The system according to claim 1 wherein the at least one gas circuit comprises a second pump device for pumping a combined gas stream (B+C) of the drift gas stream (C) and the analytical gas stream (B).

13. The system according to claim 1, wherein the exhaled breath of the patient having a concentration of an anesthetic agent, and wherein the substance concentration measured by the measurement apparatus is indicative of the concentration of the anesthetic agent in the exhaled breath of the patient.

14. The system of claim 13 wherein the anesthetic agent is Propofol.

15. A method for identifying and/or measuring a substance concentration in an exhaled breath of a patient, comprising:

obtaining a sampling gas stream (A) from the exhaled breath of the patient, and performing, by means of a measurement apparatus, an ion mobility spectrometry measurement of the sampling gas stream (A), the measurement apparatus comprising a drift detector and at least one gas circuit connected to the drift detector for guiding an analytic gas stream (B), into which a sample of the sampling gas stream (A) is injectable, the analytic gas stream (B) is injectable towards an inlet end of the drift detector and a drift gas stream (C) is injectable towards an outlet end of the drift detector, wherein the at least one gas circuit comprises a molecular sieve filter comprising a filter material for filtering the analytic gas stream (B) and the drift gas stream (C), wherein the filter material comprises zeolite NaY and wherein the at least one gas circuit forms a closed circuit for guiding the analytic gas stream (B) and the drift gas stream (C) in a closed loop, cleaning the analytic gas stream and the drift gas stream with the molecular sieve filter after their passing through the drift detector before again being injected into the drift detector.

* * * * *